United States Patent [19]
Nash et al.

[11] Patent Number: 5,700,277
[45] Date of Patent: *Dec. 23, 1997

[54] HEMOSTATIC VESSEL PUNCTURE CLOSURE WITH FILAMENT LOCK

[75] Inventors: John Nash, Downingtown; Douglas Evans, Devon, both of Pa.

[73] Assignee: Kensey Nash Corporation, Exton, Pa.

[*] Notice: The term of this patent shall not extend beyond the expiration date of Pat. No. 5,411,520.

[21] Appl. No.: 439,895

[22] Filed: May 12, 1995

Related U.S. Application Data

[63] Continuation of Ser. No. 72,293, Jun. 4, 1993, abandoned.
[51] Int. Cl.$^6$ .................................................. A61B 17/00
[52] U.S. Cl. ........................... 606/213; 128/887; 623/11
[58] Field of Search ........................... 606/213, 215; 623/1, 11; 604/15, 60, 285; 128/887

[56] References Cited

U.S. PATENT DOCUMENTS

| | | |
|---|---|---|
| 4,852,568 | 8/1989 | Kensey . |
| 5,021,059 | 6/1991 | Kensey et al. . |
| 5,061,274 | 10/1991 | Kensey . |
| 5,108,420 | 4/1992 | Marks . |
| 5,192,302 | 3/1993 | Kensey et al. ........................ 406/215 |
| 5,222,974 | 6/1993 | Kensey et al. . |
| 5,275,616 | 1/1994 | Fowler . |
| 5,282,827 | 2/1994 | Kensey et al. . |

FOREIGN PATENT DOCUMENTS

| | | |
|---|---|---|
| 90/14796 | 12/1990 | WIPO . |
| 93/08746 | 5/1993 | WIPO . |

Primary Examiner—John P. Lacyk
Attorney, Agent, or Firm—Caesar, Rivise, Bernstein, Cohen & Pokotilow, Ltd.

[57] ABSTRACT

A hemostatic closure for sealing a percutaneous puncture in a blood vessel. The puncture includes a tract leading to it from the skin of the being. The closure comprises a rigid, resorbable material anchor having a reinforcement strip therein, a compressed collagen plug, a thin filament connecting the anchor and the plug in a pulley-like arrangement, and a locking mechanism. The plug is deployed so that the anchor is pulled against the tissue contiguous with the puncture inside the artery and with the plug and the locking member within the puncture tract. Pulling on the filament moves the plug toward the anchor member to a puncture sealing position. The locking mechanism is arranged to be actuated to engage the filament in such a manner that the plug is held in the puncture sealing position. In one embodiment the locking mechanism comprises a compressible disk mounted on the filament. In another embodiment the locking mechanism comprises a notched passageway in the anchor and the filament comprises a portion having plural projections or teeth thereon adapted to slide into the notched passageway in one direction but resistant to sliding in the opposite direction. An optional spacer member may be provided interposed between the plug and the anchor to prevent the plug from entering the opening in the vessel.

43 Claims, 5 Drawing Sheets

HEMOSTATIC VESSEL PUNCTURE CLOSURE WITH FILAMENT LOCK

This is a continuation of application Ser. No. 08/072,293 filed on Jun. 4, 1993 now abandoned.

SPECIFICATION

This invention relates generally to medical devices and more particularly to hemostatic closures for sealing percutaneous incisions or punctures in blood vessels or other body vessels, ducts, or lumens.

In U.S. Pat. No. 5,021,059, which has been assigned to the same assignee as this invention, and whose disclosure is incorporated by reference herein, there is disclosed a closure device and method of use for sealing a small incision or puncture in tissue separating one portion of the body of a living being from another portion thereof, e.g., a percutaneous puncture in an artery, to prevent the flow of a body fluid, e.g., blood, through the puncture. The closure device is arranged to be used with (deployed by) an instrument which comprises a carrier in the form of a tubular member. The tubular member has a proximally located portion and a distally located portion. The latter includes an open free end arranged to be introduced through the incision or puncture. The proximately located portion of the tubular member is arranged to be located out of the body of the being when the distally located portion is extended through the incision or puncture.

The closure device comprises three components, namely, an anchor member, a sealing member, and a filament, e.g., suture. The anchor member includes a tissue engaging portion configured to pass through the puncture in one direction but resistant to passage therethrough in the opposite direction. The sealing member is formed of a hemostatic material, such as compressed collagen foam, and has a tissue engaging portion. The filament is connected between the anchor member and the sealing member in a pulley-like arrangement so that they may be moved relative to each other by the application of a pulling force on the filament.

The instrument is arranged to expel the anchor member through the puncture, e.g., into the artery, and to draw its tissue engaging portion into engagement with the tissue contiguous with the puncture. The filament extends through the instrument to a point outside the body of the being and is arranged to be drawn in the proximal direction, whereupon the portion of the filament connecting the anchor member causes the tissue engaging portion of the sealing member to move with respect to the anchor member, thereby drawing the anchor member and sealing member together. This action causes the tissue engagement portion of the sealing member to seal the puncture from the flow of fluid therethrough.

In a copending U.S. patent application Ser. No. 07/846,322, filed on Mar. 5, 1992, entitled Hemostatic Puncture Closure System and Method of Use, now U.S. Pat. No. 5,282,827, which is a Continuation-In-Part of a copending U.S. patent application Ser. No. 07/789,704, filed on Nov. 8, 1991, and of the same title, now U.S. Pat. No. 5,222,974, both of which are assigned to the same assignee as this invention, and whose disclosures are also incorporated by reference herein, there are disclosed variant systems for sealing a percutaneous incision or puncture in a blood vessel. Those systems basically comprise a closure, an introducer, and a deployment instrument including a carrier for the closure.

The closure has three basic components, namely, a sealing member, an intraarterial anchor member, and a positioning member. The sealing member is in the form of an elongated rod-like plug, e.g., a compressed hemostatic, resorbable collagen sponge or foam. This plug member is arranged for sealing the puncture. The anchor member is an elongated, stiff, low-profile member which is arranged to be seated inside the artery against the artery wall contiguous with the puncture. The anchor member is molded of non-hemostatic resorbable polymer similar to resorbable suture. The positioning member comprises a filament, e.g., a resorbable suture. The filament connects the anchor member and the collagen plug (sealing member) via a pulley-like arrangement which serves to move the plug toward the anchor member by pulling on the filament when that member is located within the interior of the artery and in engagement with the inner wall of the artery contiguous with the incision or puncture. A tamping member, forming a portion of the deployment instrument is provided to tamp the plug within the puncture tract. This action causes the plug to deform so that its diameter increases somewhat. Expansion of the plug is enhanced by the fact that it is formed of a compressed collagen so that it expands in the presence of blood within the puncture tract. The expansion of the plug within the puncture tract serves to hold it in place. The closure quickly becomes locked in place through the clotting of the hemostatic collagen plug within the puncture tract, and by tension applied to the filament via spring means forming a portion of the deployment system.

In another copending U.S. patent application Ser. No. 08/012,816, filed on Feb. 3, 1993, entitled A Hemostatic Vessel Puncture Closure System Utilizing A Plug Located Within The Puncture Tract Spaced From The Vessel, And Method of Use, now U.S. Pat. No. 5,411,520, which is assigned to the same assignee as this invention, and whose disclosure is also incorporated by reference herein, there is disclosed a system for sealing a percutaneous incision or puncture in a blood vessel or other lumen. That system includes a closure, similar in most respects to the closures disclosed in the above mentioned copending application but also having means for preventing the sealing portion of the closure from gaining access into the interior of the artery. In particular, the closure of that application includes a spacer member interposed between the anchor member and the plug member to keep the plug member in the puncture tract, but spaced from the opening in the artery.

In yet another copending U.S. patent application Ser. No. 08/064,192, filed on May 17, 1993, entitled Fail Predictable, Reinforced Anchor For Hemostatic Puncture Closure, now U.S. Pat. No. 5,312,435 which is also assigned to the same assignee as this invention, and whose disclosure is also incorporated by reference herein, there is disclosed another closure for sealing a percutaneous puncture in a blood vessel. That closure is similar in construction to the closures of the above mentioned applications except that its anchoring means comprises a generally elongated member formed of a resorbable material having reinforcing means, e.g., a filament, ribbon or mesh also formed of a resorbable material, extending along substantially the length thereof and fixedly secured thereto, e.g., molded in situ therein. The reinforcing means prevents the anchoring member from breaking apart and separating from the closure in the event of a failure in the closure or an incorrect deployment.

While the closures of the aforementioned patent applications are suitable for their intended purposes, they still may leave something to be desired from the standpoint of resistance to relative movement between the sealing member and the anchor member until the puncture is sealed and the closure locked in place through the clotting of the hemostatic collagen plug within the puncture tract.

OBJECTS OF THE INVENTION

Accordingly, it is a general object of this invention to provide a closure device and methods of use for sealing a percutaneous puncture in a vessel, duct, or lumen, and which overcomes the disadvantages of the prior art.

It is a further object of this invention to provide a vessel puncture closure device including an anchoring portion located within the vessel and an sealing portion located within the puncture tract and means for ensuring that the sealing portion and anchoring portion do not move relative to each other once properly positioned in order to facilitate the vessel sealing operation.

It is still a further object of this invention to provide a vessel puncture closure device which is simple in construction, easy to use, safe, effective, and reliable.

SUMMARY OF THE INVENTION

These and other objects of this invention are achieved by providing a closure device for sealing a percutaneous incision or puncture in a vessel, duct or lumen. The puncture comprises a tract extending through tissue overlying the opening in the vessel. The closure device comprises a anchoring means, sealing means, filament means, and a locking means.

The anchoring means is arranged to be brought into engagement with the interior tissue of the vessel contiguous with the opening in the vessel and with the sealing means being located within the puncture tract remote from the vessel. The filament means is connected between the anchoring means and the sealing means so that the sealing means may be moved in the tract toward the anchoring means to a puncture sealing position by the application of a pulling force on the filament means. The anchoring means is in engagement with the interior tissue of the vessel contiguous with the opening therein when the sealing means is in the puncture sealing position.

The locking means is actuatable to cooperate with the filament means to hold the anchoring means and the sealing means in the puncture sealing position.

In accordance with one aspect of this invention the locking means comprises a member slidably disposed on the filament means and arranged to be actuated by the application of a compressive axial force onto it to cause it to collapse radially to frictionally engage the filament means to prevent the sealing means and the anchoring means from moving relative to each other.

In accordance with another aspect of this invention the locking means comprises a filament engagement portion configured to enable the filament means to be slid with respect to the anchoring means and the sealing means in a first direction, but precluded from sliding with respect to the anchoring means and the sealing means in a second, opposite direction. In accordance with that aspect of the invention the filament means comprises a plurality of projections extending along at least a portion of the length of the filament means. The filament engagement portion of the locking means comprises a passageway in the anchoring means having at least one notch therein to receive one of the projections, with the notch being configured to enable the projections to slide therein from the first direction, but preventing any projection from sliding thereout in the second direction.

In accordance with another aspect of this invention the closure may include a spacer interposed between the anchor member and the sealing member to prohibit the sealing member from contacting the vessel wall and thereby possibly entering into the vessel where a portion could conceivably break off and flow distally and create an embolism.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein.

DETAILED DESCRIPTION OF THE PREFERRED EMBODIMENT

Referring now in greater detail to the various figures of the drawings wherein like reference characters refer to like parts, there is shown at 20 a closure device constructed in accordance with one embodiment of this invention, to seal a percutaneous puncture within a blood vessel 22, e.g., the femoral artery. The puncture includes the tract 24A leading up to the opening 24B in the wall of the vessel. By tract it is meant the passageway in the tissue located between the vessel and the skin of the being formed when the vessel is punctured.

Figure 1:
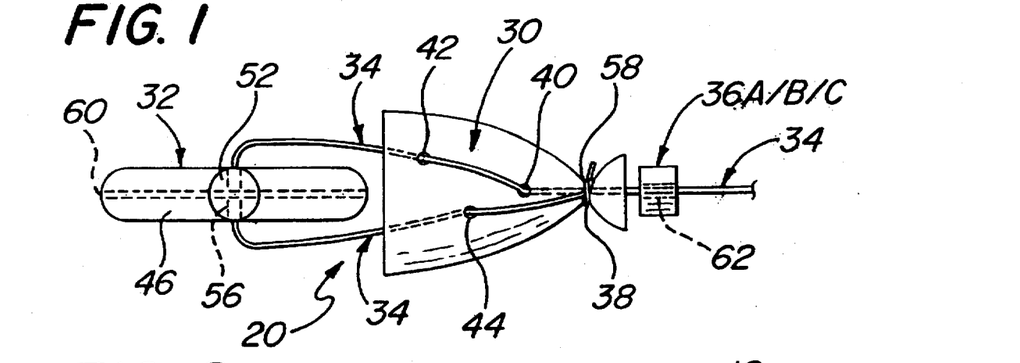
FIG. 1 is a top plan view of one embodiment of the closure device of this invention, with the sealing component of the device shown in its uncompressed state.
Figure 2:
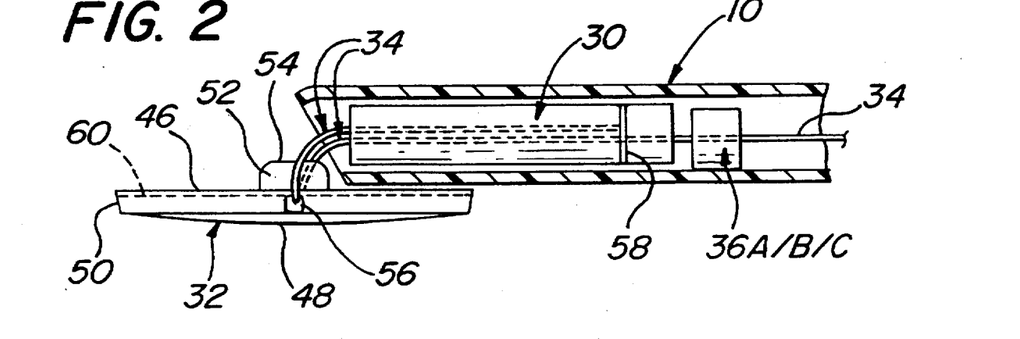
FIG. 2 is a side elevational view, partially in section, showing a portion of the deploying instrument and the closure device of FIG. 1, but with the sealing component of the closure device in its compressed state.

The embodiment of the closure 20 shown in FIG. 1 has four basic components, namely, a sealing member 30, an intraarterial anchor member 32, a positioning filament 34, and a locking member 36. Except for the locking member 36, and some aspects of the anchor member 32, the closure 20 is constructed in accordance with the teachings of the aforementioned patent applications. Thus, the sealing member or plug 30 comprises a cylindrical member formed of a compressible, resorbable, collagen foam, which is arranged to be compressed from the large diameter configuration shown in FIG. 1 to the small diameter, elongated configuration shown in FIG. 2. In the configuration of FIG. 2 the diameter of the plug is very small, e.g., 1.32 mm, and therefor suitable for disposition within a deployment instrument 10 (FIGS. 2, 5, and 8) constructed in accordance with the teachings of the aforementioned applications.

The plug 30 includes an annular recess 38 extending about its outer periphery adjacent its proximal end. Three apertures 40, 42, and 44 extend through the plug. In particular, the aperture 40 is located close to the recess 38 and diametrically through the centerline of the plug. The aperture 42 is located close to the distal end of the plug and extends transversely through the plug on one side of the centerline. The aperture 44 is located between apertures 40 and 42 and extends transversely through the plug on the other side of the centerline. These apertures serve as passageways through which the positioning filament 34 extends to connect the anchor member 32 to the plug 30.

The anchor member 32 basically comprises a thin, narrow, strip or bar of material which is preferably constructed in accordance with the teachings of the above described patent application Ser. No. 08/064,192 filed on May 17, 1993, and entitled Fail Predictable, Reinforced Anchor For Hemostatic Puncture Closure now U.S. Pat. No. 5,312,435. The strip is sufficiently rigid such that once it is in position within the artery or other vessel, duct, or lumen, it is resistant to deformation to preclude it from bending to pass back through the puncture through which it was first introduced. The anchor member 32 has a generally planar top surface 46, a radially contoured bottom surface 48, and a peripheral side surface 50. Each end of the member 32 is rounded. The side surface 50 of the anchor member 32 tapers inward slightly from its top surface 46 to its bottom surface 48 as shown in FIG. 2 to facilitate the removal of the plug from the mold for making it. A hemispherical dome-like projection 52 is located at the center of the top surface. The top of the projection 54 is slightly flat. The dome-like projection 52 is arranged to extend into the opening 24B in the blood vessel wall when the anchor member 34 is properly deployed within that vessel.

A passageway 56 of generally square profile and rounded corners extends transversely across the member 32 below the projection 52 and close to the bottom surface 48. The filament 34 is threaded through the passageway 56 as shown clearly in FIGS. 1 and 2 to connect the plug member 30 to the anchor member 32 in a pulley-like arrangement for effecting the movement of the plug component toward the anchor component once the anchor component is in its desired position in the vessel. In particular, the pulley-like connection between the anchor member and the plug member is accomplished by threading the filament 34 from a remote, externally located point into a passageway in the plug through the apertures 40 and 42 and out of the distal end of the plug and into the transversely extending passageway 56 on side of the anchor member, through that passageway to the opposite side of the anchor member (the side close to the top of the page in FIG. 1), and from there back into the plug, where it is threaded out through the aperture 44 to the opposite side of the plug, where it terminates in a loop 58 (FIG. 3) extending around the annular recess 38. The loop is secured by a knot 58A.

In order to ensure that no portion of the anchor member can break off and separate from the closure 20 when the anchor member 32 is deployed within the blood vessel, the anchor member includes a flexible strip 60, e.g., a resorbable suture, serving as reinforcing means. The strip 60 extends along the length of the elongated portion of the anchor and is fixedly secured, e.g., molded in situ, within the elongated portion of the anchor member just under the top surface 46 and above the transversely extending passageway 56.

The locking member 36 basically comprises a disk-like or washer-like member, preferably formed of a resorbable material, such as that forming the anchor member, so long as it is somewhat deformable, as will be described later. The locking member has a central passageway 62 (FIG. 1) extending therethrough and through which a proximal portion of the filament 34 extends. In the embodiment of FIG. 1 the locking member 36 is located proximally of the sealing plug 30, with a proximal portion of the positioning filament 34 passing through its central passageway 62.

The internal diameter of the central passageway 62 is larger than the external diameter of the filament 34 to enable the filament to slide with respect thereto. The locking member 36 can take any form, providing that it is constructed so that upon the application of an axial compressive force thereon a portion of it is compressed radially inward to close the passageway 62 about the filament extending therethrough, thereby frictionally engaging that filament to preclude relative movement between the locking member and the filament. In FIGS. 10–18 three suitable embodiments for the locking means are shown.

Figure 10:
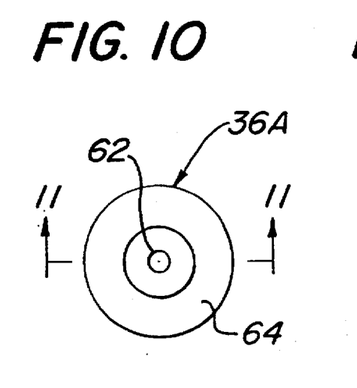
FIG. 10 is an enlarged top plan view of one embodiment of the locking component of the closure devices of FIGS. 1, 4, and 7.
Figure 11:
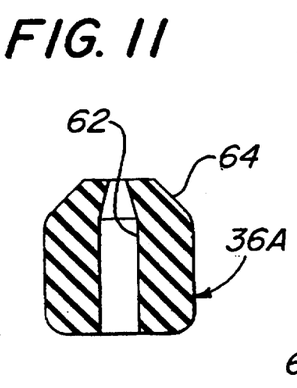
FIG. 11 is a sectional view taken along line 11—11 of FIG. 10.
Figure 12:
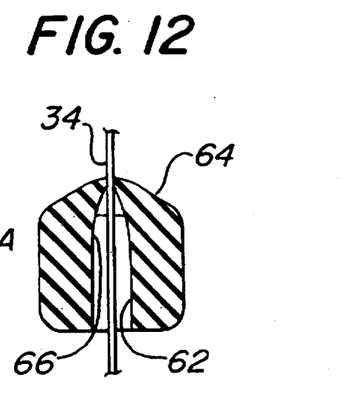
FIG. 12 is a sectional view similar to that of FIG. 11 but showing the locking component of FIG. 10 after it has been operated to prevent the sealing component and the locking component from moving relative to each other.

In particular, in FIGS. 10–12 there is shown a locking member 36A in the form of a washer having one end in the form of a tapering cone 64, with the passageway 62 extending through the washer tapering as it passes through the cone end. In this embodiment an axial compressive force, i.e., a compressive force applied parallel to the longitudinal axis of the filament 34 passing through the locking member 36A, will cause the member to deform, like shown in FIG. 12, whereupon the conical end 66 of the passageway 62 will be collapsed inward radially so that the filament will be tightly grasped to prevent relative movement between it and the locking member.

Figure 13:
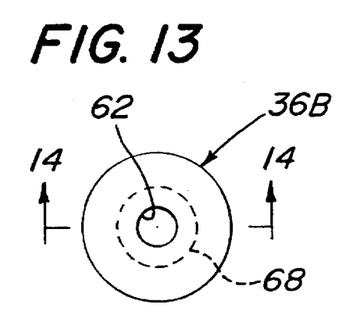
FIG. 13 is an enlarged top plan view of a second embodiment of the locking component of the closure devices of FIGS. 1, 4, and 7.
Figure 14:
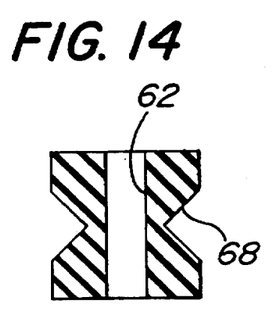
FIG. 14 is a sectional view taken along line 14—14 of FIG. 13.
Figure 15:
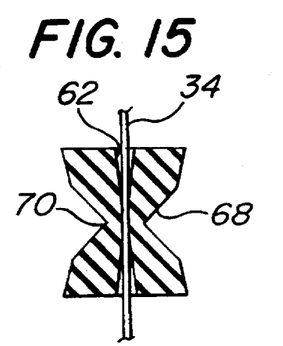
FIG. 15 is a sectional view similar to that of FIG. 14 but showing the locking component of FIG. 13 after it has been operated to prevent the sealing component and the locking component from moving relative to each other.

In FIGS. 13–15 there is shown a locking member 36B in the form of a washer having an annular tapering recess 68 extending about the outer periphery of the member at approximately the middle thereof. A central passageway 62 extends through the member 36B. In this embodiment an axial compressive force will cause the member to deform, like shown in FIG. 15, whereupon the center 70 of the passageway 62 will be collapsed inward radially so that the filament 34 will be tightly grasped to prevent relative movement between it and the locking member.

Figure 16:
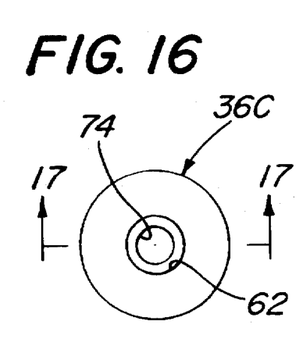
FIG. 16 is an enlarged top plan view of a third embodiment of the locking component of the closure devices of FIGS. 1, 4, and 7.
Figures 17, 18:
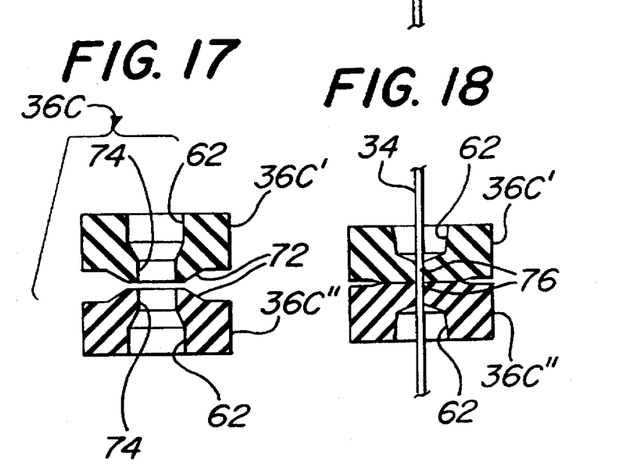
FIG. 17 is a sectional view taken along line 17—17 of FIG. 16.
FIG. 18 is a sectional view similar to that of FIG. 17 but showing the locking component of FIG. 16 after it has been operated to prevent the sealing component and the locking component from moving relative to each other.

In FIGS. 16–18 there is shown a locking member 36C in the form of a pair of washers 36C' and 36C". Each of the washers has a central passageway 62 extending therethrough. One end of each of the washers 36C' and 36C" has a conical central mesa 72 through which the passageway 62 extends. The portion 74 of the passageway extending through the mesa 72 is of a reduced diameter. The washers 36C' and 36C" are disposed so that their mesas 72 are disposed opposite each other, and with central passageways 62 axially aligned so that the filament 34 extends therethrough. In this embodiment an axial compressive force applied to the washers will cause each of them to deform, like shown in FIG. 18, whereupon the portions 74 of their passageways extending through their mesas will be collapsed inward radially at 76 so that the filament will be tightly grasped to prevent relative movement between it and the locking washers.

The closure device 20 of this invention is used in the same general manner as described in the foregoing patent applications. In particular, the physician inserts the delivery or deployment instrument 10 containing the closure into the patients' introducer sheath (not shown). On insertion, the anchor member 32 passes out of the distal end of the introducer sheath (like shown in FIG. 2) and deploys into the interior of the vessel, e.g., artery. The deployment instrument is then withdrawn from the introducer sheath until resistance is felt when the anchor member catches on the distal end of the introducer sheath. Once this occurs (and assuming that the anchor is in the correct orientation when it catches on the end of the introducer sheath) the deployment instrument and the introducer sheath are then immediately withdrawn together. This withdrawing action causes the anchor member 32 to engage (catch) on the inside of the artery contiguous with the puncture 24B in the artery wall, with the domed portion 52 of the anchor member 32 extending through the puncture 24B. The continued simultaneous retraction of the introducer sheath and the deployment instrument causes the filament 34 to pull the collagen plug 30, and the locking member 36 out of the deployment instrument 10 and into the puncture tract 24A in that order.

Figure 3:
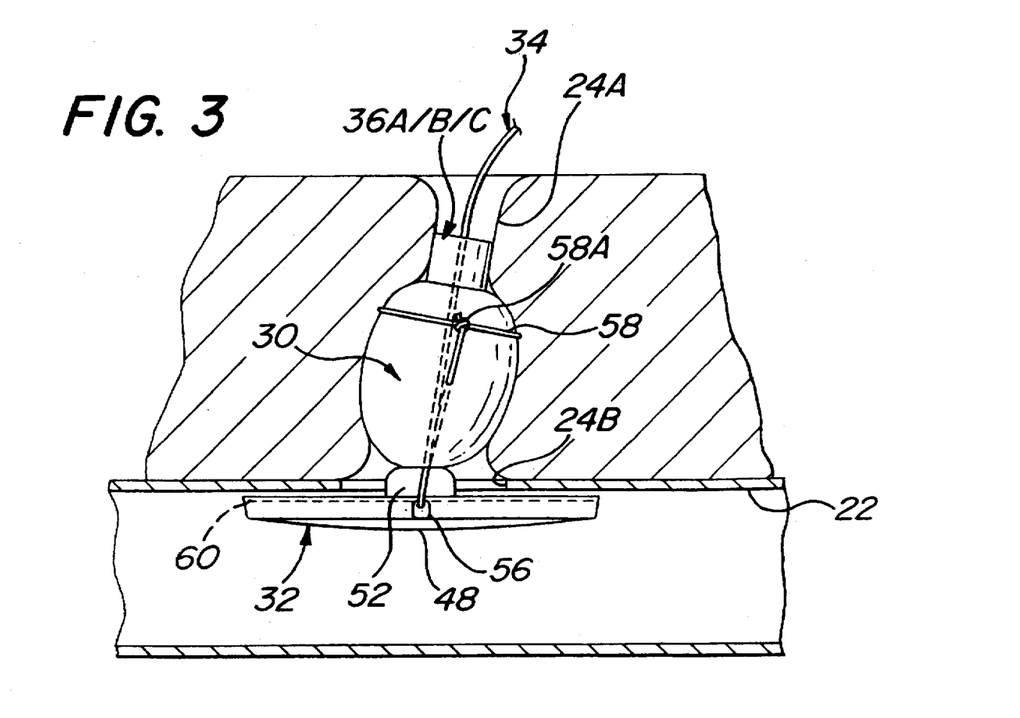
FIG. 3 is an illustration showing the closure device of FIG. 1 in place after it has sealed the percutaneous puncture in an artery.

Further, simultaneous retraction of the introducer sheath and the deployment instrument 10 brings an elongated tamping member (not shown) out of the free end of the deployment instrument. Moreover, the pulley arrangement of the filament 34 connecting the anchor member and the plug member ensures that during the retraction of the introducer sheath and the instrument, the plug member 30 is moved toward the anchor member until it engages the domed portion 52 of the anchor member 32 (which domed portion extends through the opening in the vessel wall as shown in FIG. 3). This action ensures that the plug member 30 is held away from the artery wall 22, thereby preventing any portion of the collagen plug member 30 which might break off from gaining ingress into the artery, where it could flow distally and form an embolism. Moreover, once the plug member engages the flat top of the domed portion 52 of the anchor continued retraction of the introducer sheath and deployment instrument causes the filament 34 to deform the plug 30 somewhat, i.e., causing it to deform radially outward. The existence of blood within the puncture tract 24A further contributes to the deformation of the plug member 30 since the collagen foam expands in the presence of blood.

The retraction procedure continues to pull the introducer sleeve and deployment instrument up the filament until a tag (not shown) fixedly secured onto a proximal portion of the filament is exposed. At this point the anchor member 32, the collagen plug member 30, and the locking member 36 will have been deployed, with the locking member located within the puncture tract immediately proximally of the plug 30. The plug 30 is then tamped by a tamping member (not shown) forming a portion of the deployment instrument. In particular, the user quickly compacts the collagen of the plug by gently tensioning the filament by pulling on the introducer sheath and instrument 10 in the proximal direction with one hand. The tamping member is then manually slid down the filament by the user's other hand so that it enters the puncture tract 24A and engages the proximal end of locking member 38 to cause it to slide distally into the plug member 30 to compress the plug member. A few gentle compactions are adequate to achieve the desired result, i.e., to assist the plug member 30 in spreading out and conforming to the tract 24A, thereby assisting in holding the plug in place until hemostasis occurs (which happens very quickly).

After the tamping action is completed a torsion spring (not shown) is mounted on the filament 34 between the tag and the proximal end of the tamping member. This action is necessary to maintain appropriate tension on the filament 34 while the instrument 10 is removed (i.e., the filament 34 severed). The torsion spring places continuous tension on the filament 34 and continuous compression on the tamping member. Because the locking washer 36 is located between the plug 30 and the tamping member, the washer experiences an axial compressive force, thereby compressing it and causing it to frictionally engage or lock onto the filament. This action locks the closure 20 in position so that when the deforming load, e.g., the torsion spring, is removed the closure remains in position, i.e., the plug member 30 does not move away from the anchor member 32.

The closure 20 is also locked in place by virtue of the clotting of the hemostatic collagen plug. In this regard within a few hours after deployment, the anchor member 32 will be coated with fibrin and thus attached firmly to the arterial wall, thereby eliminating the possibility of distal embolization. After approximately thirty days, only a small deposit of anchor material will remain. In fact, resorption of all components will have occurred after approximately sixty days. Moreover, since the plug 30 is formed of compressed collagen or other hydrophilic material it also expands automatically in the presence of blood within the puncture tract 24A when deployed, thereby further contributing to the plug's enlargement.

Figure 4:
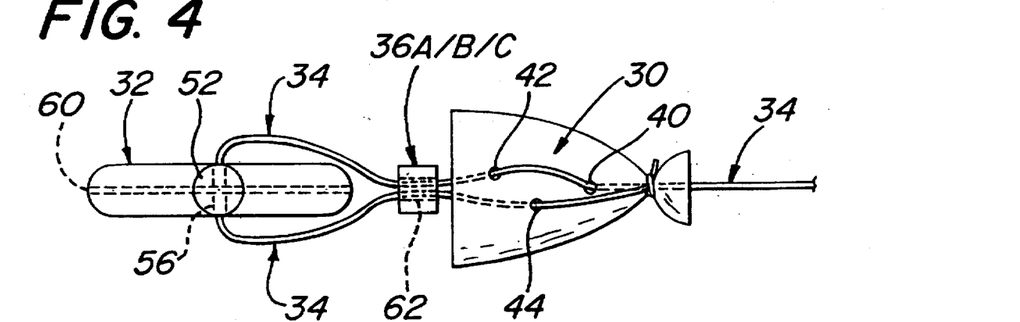
FIG. 4 is a top plan view of a second embodiment of the closure device of this invention, with the sealing component of the device shown in its uncompressed state.
Figure 5:
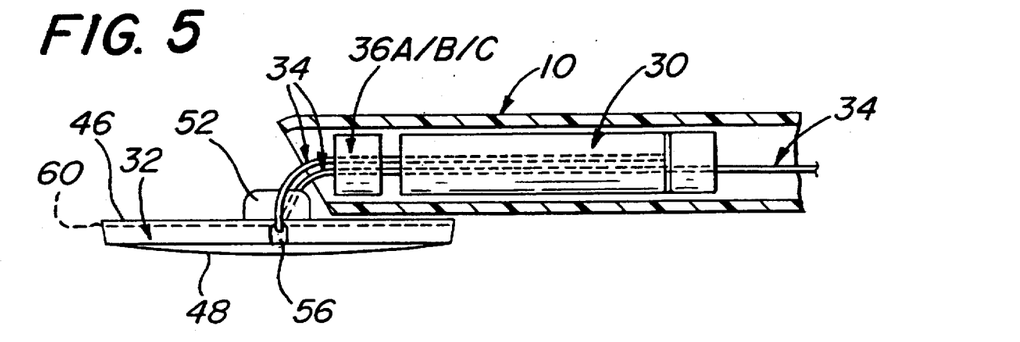
FIG. 5 is a side elevational view, partially in section, showing a portion of the deploying instrument and the closure device of FIG. 4, but with the sealing component of the closure device in its compressed state.
Figure 6:
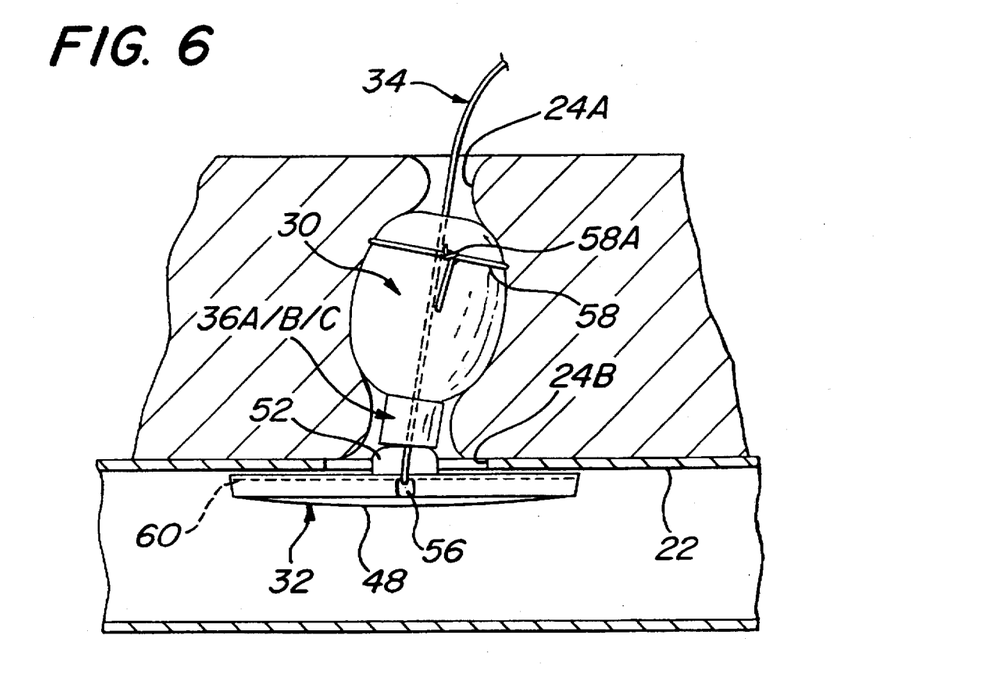
FIG. 6 is an illustration showing the closure device of FIG. 4 in place after it has sealed the percutaneous puncture in an artery.

In FIGS. 4–6 there is shown a second embodiment of the closure of this invention. That closure is identical in construction to the closure of FIGS. 1–3, except that the locking member 36 is located interposed between the plug member 30 and the anchor member 32 so that the portion of the filament 34 from the plug member to the anchor member and the portion of the filament from the anchor member back to the plug member each extend through the central opening 62 in the locking member. In this embodiment when the closure is deployed the locking member engages the top 54 of the dome portion of the anchor member, thereby holding the plug 30 further away from the opening 24B in the artery 22 than the embodiment of FIGS. 1–3, further ensuring that no portion of the plug 30 will enter the artery.

As should be appreciated by those skilled in the art even though the locking member 36 is not located proximally of the plug 30 it nevertheless still prevents the plug 30 from moving away from the anchor 32. In this regard the inward radial compression of the locking washer 36 grasps both portions of the filament extending through its central passageway 62, thereby preventing the filament from moving with respect to the anchor portion. Since the plug is fixedly secured to one end of the filament by the knotted loop 58 the plug 30 is prevented from moving with respect to the anchor 32.

Figure 7:
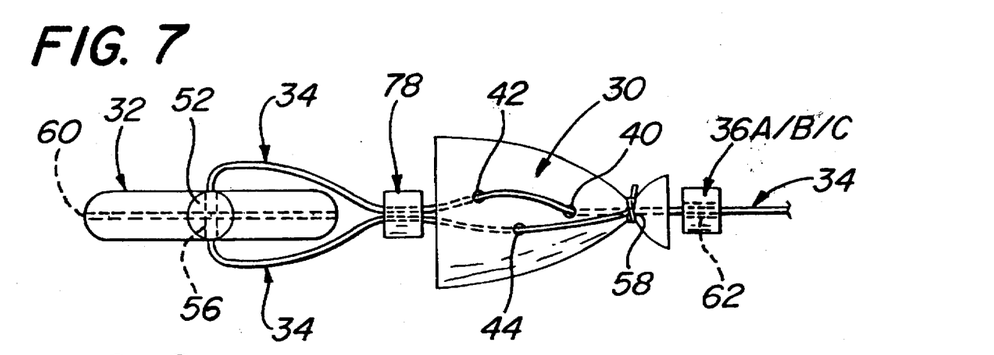
FIG. 7 is a top plan view of a third embodiment of the closure device of this invention, with the sealing component of the device shown in its uncompressed state.
Figure 8:
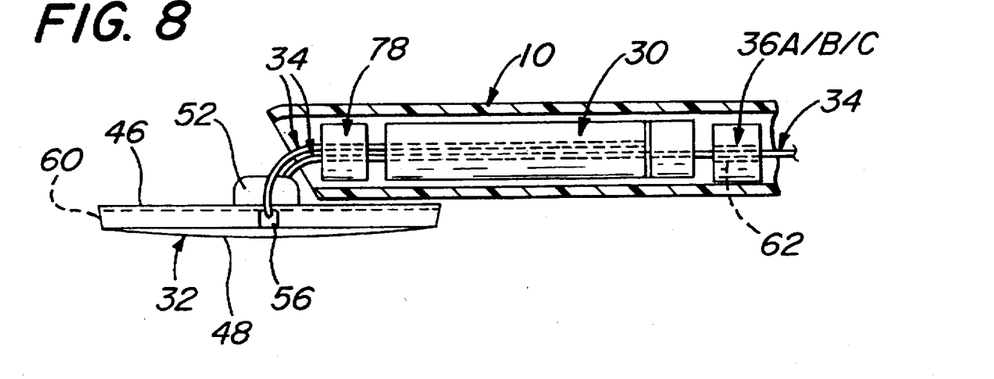
FIG. 8 is a side elevational view, partially in section, showing a portion of the deploying instrument and the closure device of FIG. 7, but with the sealing component of the closure device in its compressed state.
Figure 9:
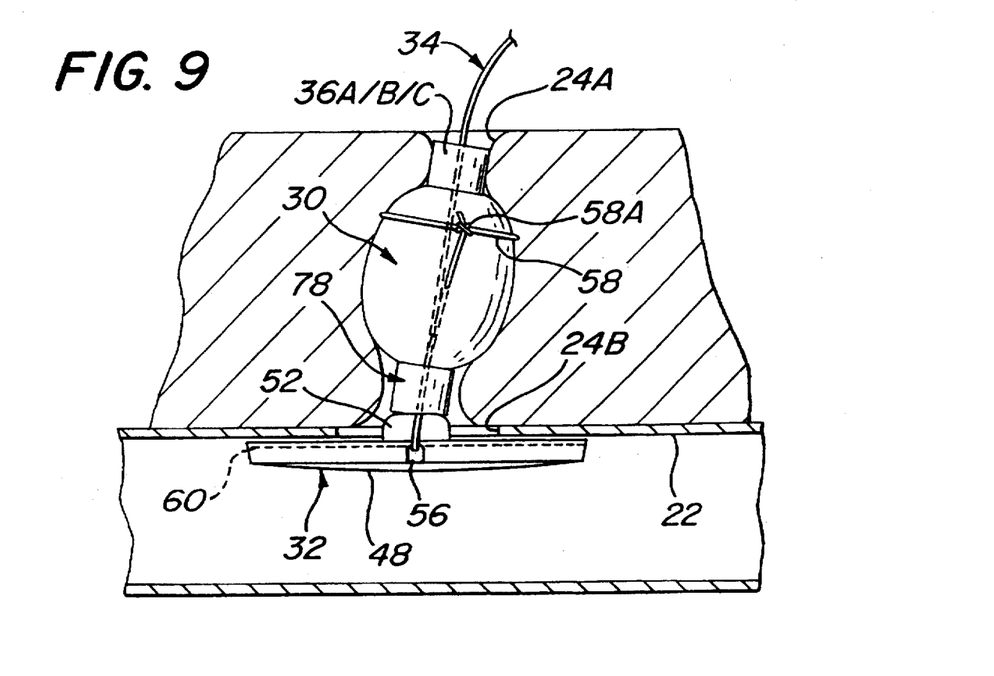
FIG. 9 is an illustration showing the closure device of FIG. 7 in place after it has sealed the percutaneous puncture in an artery.

In FIGS. 7–9 there is shown a third embodiment of the closure of this invention. That closure is identical in construction to the closure of FIGS. 1–3, except that a separate spacer component 78 is provided interposed between the plug member 30 and the anchor member 32. The spacer member 78 is a disk-like or washer-like member having at least one passageway 80 (FIG. 19) extending therethrough so that the portion of the filament 34 extending from the plug member 30 to the anchor member 32 and the portion of the filament 34 returning from the anchor member to the plug member both extend through the passageway(s) in the component 78. In this embodiment of the closure, when the closure is deployed the spacer member 78 engages the top 54 of the dome portion 52 of the anchor member 32, thereby holding the plug member 30 further away from the opening 24B in the artery 22 than the embodiment of FIGS. 1–3, thereby further ensuring that no portion of the plug will enter the artery.

The spacer member 78 is also preferably formed of a resorbable material, such as the polymer used for the anchor member. Moreover, either the spacer member 78, or the locking member 36, or the anchor member 32 may include means, like that described in the aforementioned patent applications, to enable it to be imaged radiographically to facilitate the placement of the closure at the desired situs within the patient's body or to monitor the resorption of the closure.

Figure 19:
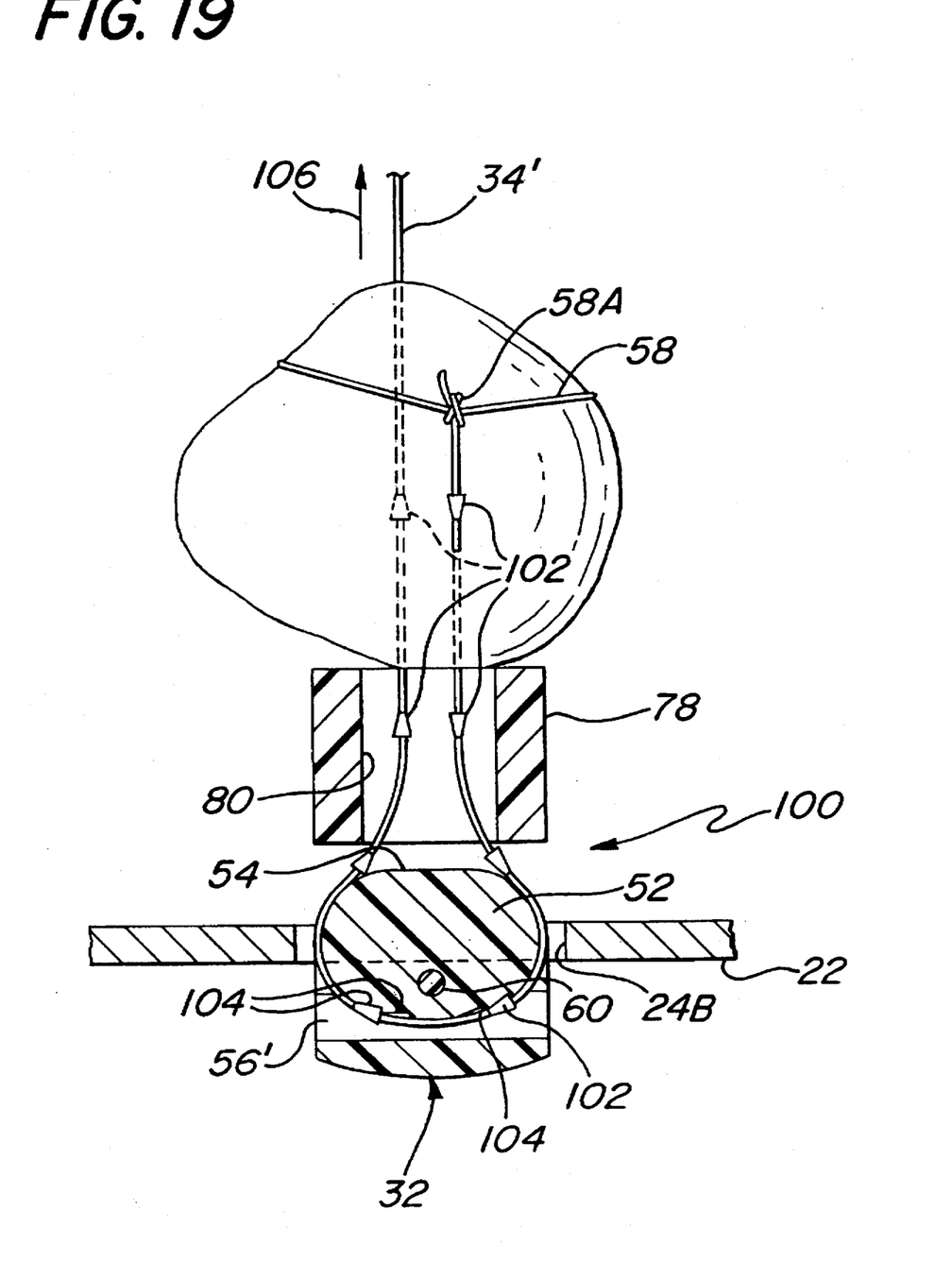
FIG. 19 is an enlarged illustration showing a fourth embodiment of closure device, partially in section, in place after it has sealed the percutaneous puncture in an artery and showing the cooperation of its locking means and the filament component of that closure.

In FIG. 19 there is shown an alternative closure 100, which while including a locking mechanism for preventing relative movement between the closure components after deployment, does not make use of any locking washer 36 like those described heretofore. In the embodiment of FIG. 19 the closure makes use of the same plug member 30, the same anchor member 32 (except for its passageway 56) and the same spacer member 78 as described above. However, the closure 100 makes use of an alternative embodiment of the filament 34 and a cooperating alternative embodiment of the anchor passageway 56. In particular the filament of the embodiment 100 of FIG. 19 is designated by reference number 34' and comprises a plurality of tooth-like projections 102 at spaced locations therealong. All of tooth-like projections include an inclined surface oriented in the same direction to enable the filament 34' to be slid in only one direction through the transverse passageway 56' in the anchor member 32. Thus, the filament can be thought of as a "one-way" filament. The passageway 56' in the anchor member 30 is similar to that described earlier except that it includes a series of tapered notches 104 adapted to receive therein one or more of the teeth 102 of the filament 34'. In particular, the notches 104 are oriented so that the filament 34 can be slid through the passageway 56' in only one direction. In this regard when moved in that one direction (shown as right-to-left in FIG. 19) the teeth 102 on the filament 34' can enter into and move out of the notches 104.

Thus, when the proximal end of the filament 34' is pulled in the direction of the arrow 106 shown in FIG. 19 (as occurs during the deployment of the closure 100) the plug member 30 is moved toward the anchor member 32 in the same manner as described earlier. However, the one-way filament prevents the plug member from moving away from the anchor member, thereby eliminating the need for a locking washer 36 to hold the plug member in place.

The spacer member 78 interposed between the plug member 30 and the anchor member 32 operates in the same manner as that described above with reference to FIGS. 7–9.

As should be appreciated from the foregoing, the deployment of the closure devices of this invention by the instruments of the aforementioned patent applications is easy, quick and reliable. Anchoring is repeatable, safe, and effective to deploy the collagen plug, and hemostasis occurs almost instantaneously, e.g., in 15 seconds or less.

Without further elaboration the foregoing will so fully illustrate our invention that others may, by applying current or future knowledge, adopt the same for use under various conditions of service.

What is claimed is:

1. A closure device for sealing a percutaneous puncture in the wall of a blood vessel, the puncture being an opening in the wall of the blood vessel and a tract contiguous with the opening and extending through tissue overlying the vessel, said closure device comprising anchoring means, sealing means, filament means having a longitudinal axis, and locking means, said anchoring means being adapted to be brought into engagement with interior tissue of the vessel contiguous with the opening for anchoring therein and with said sealing means adapted to be inserted within the tract, said filament means including a portion connected to said sealing means and extending along a portion thereof so as to be through the tract to said anchoring means and being coupled to said anchoring means in such a manner that said sealing means may be moved in the tract toward said anchoring means to a puncture sealing position by the application of a pulling force on said filament means, whereupon said portion of said filament means is placed in tension, said anchoring means adapted to be in engagement with the interior tissue of the vessel contiguous with the opening when said sealing means is in the puncture sealing position, said locking means comprising a member temporarily slidably mounted on said filament means and actuatable within the tract so that when actuated it is permanently fixedly secured to said filament means to maintain tension in said portion of said filament means and to permanently engage said sealing means to hold said sealing means in the puncture sealing position and thereby prevent said sealing means from moving away from said anchoring means.

2. The closure device of claim 1 wherein said locking member is actuated by the application of a compressive force applied thereto parallel to the longitudinal axis of said filament means.

3. The closure device of claim 2 wherein said locking means comprises a disk-like member having at least one passageway extending therethrough, said filament means extending through said passageway, said passageway closing about said filament means extending therethrough upon the application of said compressive force to said locking means.

4. The closure device of claim 1 wherein said anchoring means, said sealing means, said filament means, and said locking means are each formed of a resorbable material.

5. A closure device for sealing a percutaneous puncture in the wall of a blood vessel, the puncture being an opening in the wall of the blood vessel and a tract contiguous with the opening and extending through tissue overlying the vessel, said closure device comprising anchoring means, sealing means, filament means having a longitudinal axis, locking means, and spacer means, said anchoring means being adapted to be brought into engagement with the interior tissue of the vessel contiguous with the opening for anchoring therein and with said sealing means adapted to be located within the tract, said filament means being connected between said anchoring means and said sealing means so that said sealing means is moved in the tract toward said anchoring means to a puncture sealing position by the application of a pulling force on said filament means, said anchoring means adapted to be in engagement with the interior tissue of the vessel contiguous with the opening when said sealing means is in the puncture sealing position, said spacer means being located interposed between said sealing means and said anchoring means and movable with respect to said anchoring means for prohibiting said sealing means from contacting the vessel wall, said locking means cooperating with said filament means to hold said anchoring means and said sealing means in the puncture sealing position.

6. The closure device of claim 5 wherein said anchoring means, said sealing means, said filament means, and said locking means are each formed of a resorbable material.

7. The closure device of claim 2 wherein said locking means is located proximally of said sealing means.

8. The closure device of claim 7 wherein said anchoring means having a passageway, said filament means comprises a first end fixedly secured to said sealing means, an intermediate portion extending from said sealing means through said passageway in said anchoring means and back to said sealing means, and a proximal portion extending along said sealing means through said locking means and out of the percutaneous puncture, and wherein said locking means when compressed securely engages said proximal portion of said filament means to prevent relative movement between said sealing means and said anchoring means.

9. The closure device of claim 2 wherein said locking means is located interposed between said sealing means and said anchoring means.

10. The closure device of claim 9 wherein said anchoring means having a passageway, said filament means comprises a first end fixedly secured to said sealing means, an intermediate portion extending from said sealing means through said passageway in said anchoring means through said locking means and back to said sealing means, and a proximal portion extending along said sealing means and out of the percutaneous puncture, and wherein said locking means when compressed securely engages said intermediate portion of said filament means to prevent relative movement between said sealing means and said anchoring means.

11. The closure device of claim 9 wherein said locking means also serves as a spacer prohibiting said sealing means from contacting said vessel wall.

12. The closure device of claim 1 wherein said anchoring means additionally comprises reinforcing means for preventing said anchoring means from breaking apart.

13. The closure device of claim 1 wherein said locking means comprises a filament engagement portion configured to enable said filament means to be slid with respect to said anchoring means and said sealing means in a first direction, but precluded from sliding with respect to said anchoring means and said sealing means in a second, opposite direction.

14. A closure device for sealing a percutaneous puncture in the wall of a blood vessel, the puncture being an opening in the wall of the blood vessel and a tract contiguous with the opening and extending through tissue overlying the vessel, said closure device comprising anchoring means, sealing means, filament means having a longitudinal axis, and locking means, said anchoring means adapted to be brought into engagement with interior tissue of the vessel contiguous with the opening for anchoring therein and with said sealing means adapted to be located within the tract, said filament means being connected between said anchoring means and said sealing means so that said sealing means is moved in the tract toward said anchoring means to a puncture sealing position by the application of a pulling force on said filament means, said anchoring means adapted to be in engagement with the interior tissue of the vessel contiguous with the opening when said sealing means is in said puncture sealing position, said filament means comprising a plurality of projections extending along at least a portion of the length of said filament means, said locking means comprising a filament engagement portion configured to enable said filament means to be slid with respect to said anchoring means and said sealing means in a first direction, but precluded from sliding with respect to said anchoring means and said sealing means in a second, opposite direction to hold said anchoring means and said sealing means in said puncture sealing position, said filament engagement portion of said locking means comprising a passageway in said anchoring means having at least one notch therein to receive one of said plurality of projections, said notch being configured to enable said plurality of projections to slide therein from said first direction, but preventing any one of said plurality of projections from sliding thereout in said second direction.

15. The closure device of claim 14 wherein said filament means comprises a first end fixedly secured to said sealing means, an intermediate portion having said projections thereon and extending from said sealing means through said passageway in said anchoring means and back to said sealing means, and a proximal portion extending along said sealing means and out of said percutaneous puncture.

16. The closure device of claim 13 wherein said anchoring means, said sealing means, said filament means, and said locking means are each formed of a resorbable material.

17. The closure device of claim 14 additionally comprising spacer means located interposed between said sealing means and said anchoring means, said spacer means for prohibiting said sealing means from contacting the vessel wall.

18. The closure device of claim 17 wherein said anchoring means, said sealing means, said filament means, said locking means, and said spacer means are each formed of a resorbable material.

19. The closure device of claim 1 wherein a portion of said closure device comprises a radio-opaque material.

20. A method of sealing a small percutaneous puncture in a blood vessel of a living being, said percutaneous puncture being an opening in the vessel and a tract contiguous therewith extending through tissue overlying the vessel, said method comprising:

(a) providing a closure comprising anchoring means, sealing means, filament means, and locking means, said filament means having a first portion secured to said sealing means, a second portion coupled to said anchoring means, and a third portion, (b) movably coupling said anchoring means, said sealing means, and said locking means together by said filament means, (c) inserting said anchoring means within the vessel in engagement with the interior of the vessel contiguous with the opening so that said sealing means and said locking means are within the tract, with said second portion of said filament means extending along said sealing means from said first portion to said anchoring means, and with said third portion of said filament means extending from said anchoring means back through the tract to outside the body of the being, (d) operating said filament means by pulling on said third portion to move said sealing means toward said anchoring means to cause said sealing means to seal said percutaneous puncture, and wherein said pulling on said third portion causes said filament means to apply tension to said second portion of said filament means, and (e) actuating said locking means within the tract to cause said locking means to engage at least a portion of said filament means in such a manner that the tension is maintained on said second portion of said filament means, and to cause said locking means to permanently engage said sealing means, whereupon said sealing means and said anchoring means are prevented from moving relative to each other.

21. The method of claim 20 wherein said locking means comprises a locking member slidably mounted on said filament means, and wherein actuating of said locking means comprises applying a compressive force to said locking member in a direction parallel to the longitudinal axis of said filament means to cause said locking member to engage at least one portion of said filament means, whereupon said sealing means and said anchoring means are prevented from moving relative to each other.

22. The method of claim 20 wherein said locking means comprises a filament engagement portion configured to enable said filament means to be slid with respect to said anchoring means and said sealing means in a first direction, but precluded from sliding with respect to said anchoring means and said sealing means in a second, opposite direction, and wherein actuating of said locking means comprises pulling on said third portion of said filament means to cause said sealing means to move toward said anchoring means in said first direction.

23. A method of sealing a small percutaneous puncture in a blood vessel of a living being, the percutaneous puncture being an opening in the vessel and a tract contiguous therewith extending through tissue overlying the vessel, said method comprising:

(a) providing a closure comprising anchoring means, sealing means, filament means, locking means, and spacer means, (b) movably coupling said anchor means, said sealing means, and said locking means together by said filament means, (c) providing said spacer means interposed between said anchoring means and said sealing means, (d) inserting said anchoring means within the vessel in engagement with the interior of the vessel contiguous with the opening and with said sealing means, said locking means, and said spacer means within the tract, (e) operating said filament means to move said sealing means and said spacer means toward said anchoring means but remote from the vessel to seal the percutaneous puncture, said spacer means preventing said sealing means from gaining ingress into the vessel via the opening, and (f) actuating said locking means within the tract to cause said locking means to engage said filament means in such a manner that said sealing means and said anchoring means are prevented from moving relative to each other.

24. A method of sealing a small percutaneous puncture in a blood vessel of a living being, the percutaneous puncture being an opening in the vessel and a tract contiguous therewith extending through tissue overlying the vessel, said method comprising:

(a) providing a closure comprising anchoring means, sealing means, filament means, locking means, and spacer means, (b) movably coupling said anchor means, said sealing means, and said locking means together by said filament means, (c) inserting said anchoring means within the vessel in engagement with the interior of the vessel contiguous with the opening and with said sealing means, said locking means, and said spacer means within the tract so that said sealing means is located remote from the vessel and with said spacer means interposed between said anchoring means and said sealing means to prevent said sealing means from gaining ingress into the vessel via the opening, (d) operating said filament means to move said sealing means and said spacer means toward said anchoring means to seal the percutaneous puncture, and (e) actuating said locking means within the tract to cause said locking means to engage said filament means in such a manner that said sealing means and said anchoring means are prevented from moving relative to each other, said locking means comprising a member slidably mounted on said filament means, and wherein actuating of said locking means comprises applying a compressive force to said member in a direction parallel to the longitudinal axis of said filament means to cause said member to engage said filament means, whereupon said filament means and said anchoring means are prevented from moving relative to each other.

25. A method of sealing a small percutaneous puncture in a blood vessel of a living being, the percutaneous puncture being an opening in the vessel and a tract contiguous therewith extending through tissue overlying the vessel, said method comprising:

(a) providing a closure comprising anchoring means, sealing means, filament means, locking means, and spacer means, (b) movably coupling said anchor means, said sealing means, and said locking means together by said filament means, (c) inserting said anchoring means within the vessel in engagement with the interior of the vessel contiguous with the opening and with said sealing means, said locking means, and said spacer means being located within the tract so that said sealing means is located remote from the vessel and with said spacer means interposed between said anchoring means and said sealing means to prevent said sealing means from gaining ingress into the vessel via the opening, said locking means comprising a filament engagement portion configured to enable said filament means to be slid with respect to said anchoring means and said sealing means in a first direction, but precluded from sliding with respect to said anchoring means and said sealing means in a second, opposite direction, (d) operating said filament means to move said sealing means toward said anchoring means to seal the percutaneous puncture, and (e) actuating said locking means within the tract by pulling on said filament means to cause said sealing means to move toward said anchoring means in said first direction and with said locking means engaging said filament means in such a manner that said sealing means and said anchoring means are prevented from moving relative to each other.

26. A closure device for sealing a percutaneous puncture in the wall of a blood vessel, the puncture being an opening in the wall of the vessel and a tract contiguous with the opening and extending through tissue overlying the vessel, said closure device comprising anchoring means, sealing means, filament means having a longitudinal axis, and spacer means, said anchoring means adapted to be brought into engagement with interior tissue of the vessel contiguous with the opening for anchoring therein and with said sealing means adapted to be located within the tract remote from the vessel, said filament means being connected between said anchoring means and said sealing means so that said sealing means is moved in the tract toward said anchoring means to a puncture sealing position wherein the blood from the blood vessel is prevented from passing through the tract, said anchoring means being adapted to be in engagement with interior tissue of the vessel contiguous with the opening when said sealing means is in said puncture sealing position, said spacer means being movable with respect to said anchoring means and being located interposed between said sealing means and said anchoring means when said sealing means is in said puncture sealing position to prohibit said sealing means from contacting said vessel wall.

27. The closure device of claim 26 wherein said anchoring means, said sealing means, said filament means, and said spacer means are each formed of a resorbable material.

28. The closure device of claim 26 wherein said spacer means also serves as a locking means prohibiting said sealing means from moving with respect to said anchoring means.

29. The closure device of claim 26 wherein said anchoring means additionally comprises reinforcing means for preventing said anchoring means from breaking apart.

30. The closure device of claim 26 wherein a portion of said closure device comprises a radio-opaque material.

31. The closure device of claim 26 wherein said spacer means is disposed on said filament means.

32. The closure device of claim 31 wherein said spacer means is disposed on said filament means.

33. A method of sealing a small percutaneous puncture in the wall of a blood vessel of a living being, the percutaneous puncture being an opening in the wall of the vessel and a tract contiguous therewith extending through tissue overlying the vessel, said method comprising:

(a) providing a closure comprising anchoring means, sealing means, filament means, and spacer means, (b) movably coupling said anchoring means, said spacer means, and said sealing means together by said filament means, (c) providing said spacer means interposed between said anchoring means and said sealing means, and (d) inserting said anchoring means within the vessel in engagement with the interior of the vessel contiguous with the opening and with said sealing means and said spacer means within the tract, whereupon said spacer means prohibits said sealing means from contacting said vessel wall.

34. The method of claim 33 additionally comprising the step of:

(e) operating said filament means to move said sealing means toward said anchoring means but remote from the vessel to seal the percutaneous puncture, with said spacer means preventing said sealing means from gaining ingress into the vessel via the opening.

35. The method of claim 33 wherein said anchoring means, said sealing means, said filament means, and said spacer means are each formed of a resorbable material, whereupon said anchoring means, said sealing means, said filament means, and said spacer means are resorbed within the body of said being.

36. The method of claim 33 wherein a portion of said closure device comprises a radio-opaque material, and wherein said method additionally comprises the step of determining the location of said closure device by radiographic imaging of said radio-opaque material.

37. A closure device for sealing a percutaneous puncture in the wall of a blood vessel, the puncture being a tract contiguous with the opening and extending through tissue overlying the vessel, said closure device comprising anchoring means, sealing means, filament means having a longitudinal axis, and locking means, said anchoring means adapted to be brought into engagement with interior tissue of the vessel contiguous with the opening for anchoring therein and with said sealing means adapted to be located within the tract, said filament means including a first portion connected to said sealing means, a second portion extending along a portion of the sealing means through the tract to said anchoring means where it is coupled thereto, and a third portion extending from said anchoring means back through the tract to outside the body of the being, said filament means being coupled to said anchoring means in such a manner that said sealing means is moved in the tract toward said anchoring means to a puncture sealing position by the application of a pulling force on said third portion of said filament means, said anchoring means adapted to be in engagement with the interior tissue of the vessel contiguous with the opening when said sealing means is in the puncture sealing position, said locking means being arranged for location within the tract proximally of said sealing means and being actuable within the tract so that when actuated it engages at least one portion said filament means and at least one portion of said sealing means to hold said anchoring means and said sealing means in the puncture sealing position.

38. The closure device of claim 37 wherein said locking means comprises a member slidably mounted on said filament means, and wherein said locking means is actuatable by the application of a compressive force applied thereto parallel to the longitudinal axis of the filament means.

39. The closure device of claim 37 wherein said locking means comprises a disk-like member having at least one passageway extending therethrough, said filament means extending through said passageway, said passageway closing about said filament means extending therethrough upon the application of the compressive force to said locking means.

40. The closure device of claim 37 additionally comprising spacer means located interposed between said sealing means and said anchoring means, said spacer means for prohibiting said sealing means from contacting the vessel wall.

41. The closure device of claim 1 wherein said locking member is a unitary member.

42. The closure device of claim 1 wherein said locking member frictionally engages said filament means upon being actuated.

43. The closure device of claim 2 wherein said locking member frictionally engages said filament means upon being actuated.

* * * * *